United States Patent [19]
Lajos

[11] 4,057,067
[45] Nov. 8, 1977

[54] ATRIOVENTRICULAR ELECTRODE

[76] Inventor: Thomas Z. Lajos, 2454 W. Oakfield Road, Grand Island, N.Y. 14072

[21] Appl. No.: 674,235

[22] Filed: Apr. 6, 1976

[51] Int. Cl.² .............................................. A61N 1/04
[52] U.S. Cl. .................................. 128/418; 128/419 P
[58] Field of Search ...................... 128/2.05 R, 2.06 E, 128/2.06 R, 404, 418, 419 P

[56] References Cited

U.S. PATENT DOCUMENTS

| 3,348,548 | 10/1967 | Chardack | 128/418 |
|---|---|---|---|
| 3,729,008 | 4/1973 | Berkovits | 128/419 P |
| 3,865,118 | 2/1975 | Burgs | 128/419 P |
| 3,890,977 | 6/1975 | Wilson | 128/419 P |
| 3,915,174 | 10/1975 | Preston | 128/419 P |
| 3,949,757 | 4/1976 | Sabel | 128/419 P |

Primary Examiner—William E. Kamm
Attorney, Agent, or Firm—Diller, Brown, Ramik & Wight

[57] ABSTRACT

This disclosure relates to an atrioventricular electrode for the purpose of electrically stimulating the heart, for example, in conjunction with a pacemaker. The atrioventricular electrode includes a ventricular component and an atrial component, both carried by a common body. The atrial component, in its original form assumes a generally J-shaped configuration so that it may hook onto the atrial appendage at the time the ventricular component has the electrode thereof firmly engaged against the right ventricular wall. Restraining means are provided for, during the insertion of the atrioventricular electrode to restrain the atrial component in a substantially straight line relationship adjacent the ventricular component so as to facilitate the insertion of the atrioventricular electrode. The restraining means is preferably in the form of a stylet utilized for the purpose of positioning the atrioventricular electrode and which stylet, when withdrawn, permits the bending of the atrial component back to its original J-shaped configuration.

8 Claims, 5 Drawing Figures

U.S. Patent  Nov. 8, 1977  4,057,067
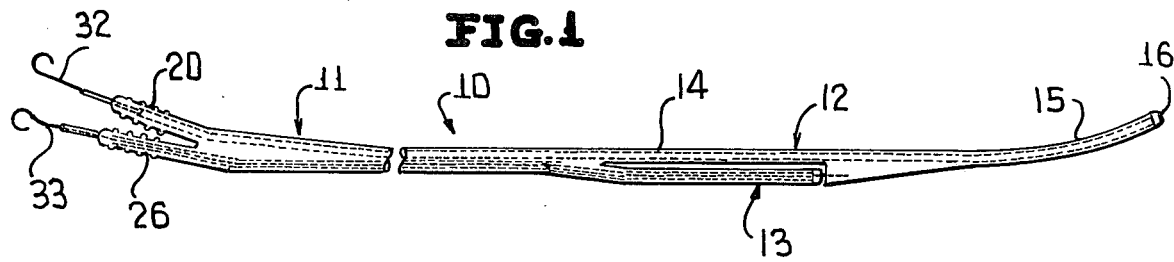
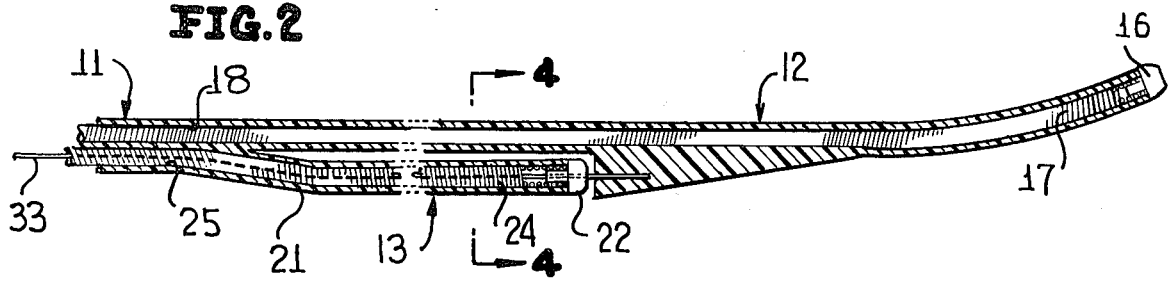
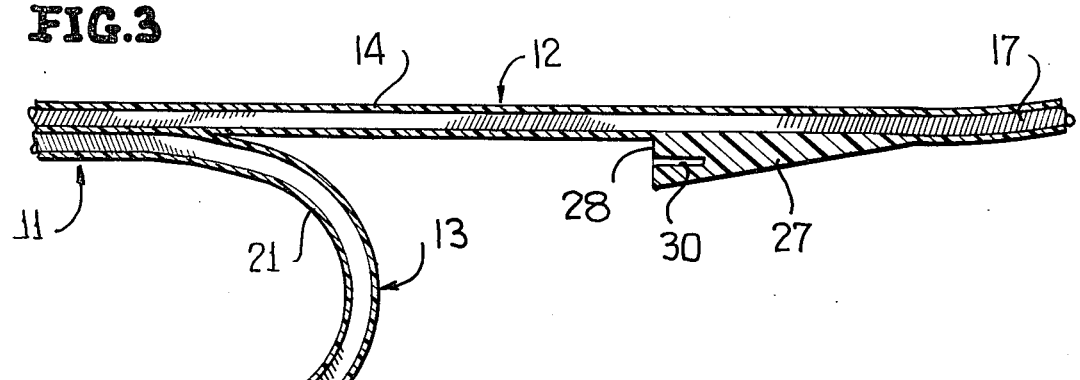
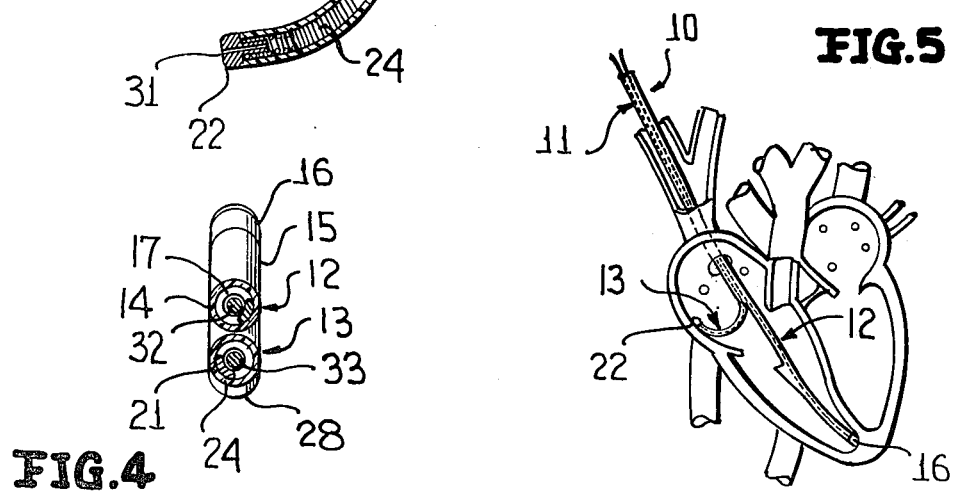

ATRIOVENTRICULAR ELECTRODE

This invention relates in general to new and useful improvements in electrode components to be utilized in conjunction with pacemakers and like devices for imparting to the heart a regulating shock.

Symptomatic patients who have marked sinus bradycardia without delay in atrioventricular conduction are often treated by ventricular pacing with demand pacemakers. Unfortunately, during ventricular pacing the atrial contribution to cardiac output is lost. This impairs effort tolerance and may produce congestive heart failure in patients with poor ventricular function. The advantages of atrial pacing are very real, both in the tachycardia/bradycardia syndrome and in overpacing ventricular tachyarrhythmias. Unfortunately, a permanent atrial pacing system usually requires suturing electrodes to the left or right atrium and necessitates a thoracotomy in patients who are often aged or very ill.

Transvenous atrial pacing with a permanently implanted pacemaker can be achieved in two ways. First, a bipolar electrode can be placed in the coronary sinus. However, we have no experience with a permanent system that uses coronary sinus pacing. Second, a transvenous electrode may be fixed in the right atrium in various positions via the right atrial appendage. The problem with this method has been that electrode instability necessitates frequent repositioning of the electrode. This system has been found unstable and unreliable in cases where temporary electrodes are used.

As a result of the foregoing, there has been developed an electrode which can be easily introduced transvenously with local anesthesia and which allows both atrial and ventricular pacing or sequential pacing as the need arises.

With the above and other objects in view that will hereinafter appear, the nature of the invention will be more clearly understood by reference to the following detailed description, the appended claims and the several views illustrated in the accompanying drawings:

IN THE DRAWINGS:

FIG. 1 is a side elevational view of the electrode of this invention with the atrial component thereof in its restraining position, ready for insertion into a patient.

FIG. 2 is an enlarged fragmentary longitudinal sectional view of the right half of the electrode of FIG. 1 and shows more specifically the manner in which the atrial component is restrained against the forming to its natural J-shaped configuration.

FIG. 3 is a fragmentary longitudinal sectional view similar to that of FIG. 2 wherein the atrial component has been released and it has bent back to its normal J-shaped configuration.

FIG. 4 is an enlarged fragmentary transverse sectional view taken along line 4—4 of FIG. 2 and shows more specifically the configurations of the ventricular and atrial components.

FIG. 5 is a schematic view showing the electrode positioned within a heart.

Referring now to the drawings in detail, it will be seen that the atrioventricular electrode is generally identified by the numeral 10 and for descriptive purpose may be divided into three basic components. These components are a common body 11, a ventricular component 12 and an atrial component 13.

The ventricular component 12 is in the form of an elongated tube 14 which has a slightly curved terminal portion 15 terminating in a ventricular electrode tip 16. As is best shown in FIG. 2, the ventricular component 12 also includes a spiral wound conductor 17 which has its right end electrically connected to the tip 16. The common body 11 has a bore 18 extending therethrough as an extension of the bore of the tube 14 with the conductor 17 extending through the common body and terminating in a standard pacemaker connector 20.

The atrial component 13 also includes an elongated tube 21 which terminates in an atrial electrode tip 22. Extending through the tube 21 is a spiral wound conductor 24 which is electrically connected to the tip 22. The tube 21 has a bore which is a continuation of a bore 25 in the common body 11 with the conductor 24 extending through the common body 11 and terminating in a standard pacemaker connector 26. At this time it is pointed out that it is preferred that the tips 16 and 22 be formed of a platinum-irridium alloy while the conductors 17, 24 are preferably formed of nickel alloy wire. The tubing 14 and 21 as well as the other exterior components of the device, including the common body 11, are preferably formed of a clean room grade, transparent silicone rubber.

In a typical atrioventricular electrode, it is preferred that the common body have an overall length of 38 cm while the atrial component has an overall length of 8 to 10 cm. On the other hand, the ventricular component preferably has a length between 18 and 20 cm. when the electrode is to be utilized with an adult. This dimension of the ventricular component arises for the proper positioning of the atrial component.

The ventricular component 12, starting in spaced relation to the tip 16, is provided with an integral enlargement 27 which flares towards the common body 11 and terminates in a shoulder or flange 28. The projection 27, at the shoulder 28, is of a sufficient size so as to completely shield the atrial component 13 when it is disposed parallel to the ventricular component, as shown in FIGS. 1 and 2. The projection 27 is provided with an aperture 30 which opens through the shoulder 28.

At this time it is pointed out that the tip 22 of the atrial component 13 is also provided with an aperture 31 opening therethrough.

Referring once again to FIG. 1, it will be seen that in order to position the atrioventricular electrode, it is provided with two removable stylets 32, 33. The stylet 32 extends through the common body 11 and through the ventricular component 12 to the tip thereof so as to facilitate properly positioning the tip 16 with respect to the right ventricular wall of the patients heart, as shown in FIG. 5. The stylet 33 has a different function. Prior to the placing of the atrioventricular electrode in a patient, the atrial component 13 is forcably removed from its projecting J-shaped configuration of FIG. 3 to a position parallel to the ventricular component 12, as shown in FIGS. 1 and 2. The stylet 33 is projected through the aperture 31 in the tip 22 and further beyond into the aperture 30, as is clearly shown in FIG. 2. Thus the stylet 33 functions to restrain the atrial component against movement to its natural position of FIG. 3.

As in apparent from FIG. 5, when the stylet 33 is withdrawn, the atrial component 13 will immediately bend back to its normal J-shaped configuration and become hooked onto the atrial appendage.

ELECTRODE INTRODUCTION

The method of introducing the electrode into the right ventricle is the same as that used for other transvenous electrodes. A cutdown is performed with local anesthesia and the electrodes is inserted with fluoroscopic control via either the cephalic vein or the external jugular vein. The position of the electrode in the right ventricle is verified by fluoroscopy. Once an area of relatively low-threshold ventricular pacing has been established, the atrial stylet may be withdrawn. The atrial part of the electrode will assume its J-shaped configuration of FIG. 3, as shown in FIG. 5 and will lie against the right atrial wall. Threshold for atrial stimulation is then established with the atrial electrode tip, the position of which is adjusted so that the atrial component lies either in the right atrial appendage or against the right atrial wall. Care must be taken not to lose the ventricular fixation position, which is important not only for maintaining an acceptable pacing threshold, but also for providing the double fixation necessary to ensure long-term electrode stability.

The electrode has the unique advantage of being relatively fixed in both the atrium and ventricle with advancement being prevented by the right ventricular wall and retraction being hindered by the J-shape of the atrial component and the hooking of the tip thereof onto the atrial appendage. The length of the ventricular component is important and it has been determined that an average length of 18 to 20 cm. in adults is the most desirable by measuring the length of the transvenous pacemaker electrode from the tip of the right ventricle to the point on the x-ray film where the electrode appears to enter the right atrium.

The main advantage of the atrial ventricular electrode is that it can be implanted with ease and speed in critically ill patients without the need of even a limited thoracotomy. The double fixation in both the atrium and ventricle assures stability of the pacing system. The electrode apparently has the normal longevity of the presently used transvenous electrodes. As a further advantage, the system may eventually be convertible to ventricular pacing should the need arise. The electrode lends itself to all modalities of sensing and pacing in the right side of the heart.

Although a preferred embodiment of the electrode has been specifically illustrated and described herein, it is to be understood that minor variations may be made therein without departing from the spirit and scope of the invention, as defined by the appended claims.

I claim:

1. An atrioventricular electrode comprising a common body, a ventricular component extending from said common body as a continuation thereof, said ventricular component terminating remote from said common body in a ventricular electrode tip, an atrial component extending from said common body and normally reversely turning relative to said common body to assume a generally J-shaped configuration, said atrial component terminating remote from said common body in an atrial electrode tip, and releasable means carried cooperatively by said atrial component and said ventricular component for temporarily retaining said atrial component as a generally straight line continuation of said common body and generally parallel to said ventricular component.

2. An atrioventricular electrode according to claim 1 with said releasable means being in the form of a stylet extending from said atrial component through said common body, and a portion of said ventricular component.

3. An atrioventricular electrode according to claim 2 wherein said stylet extends beyond said atrial component into said portions of said ventricular component.

4. An atrioventricular electrode comprising a common body, a ventricular component extending from said common body as a continuation thereof, said ventricular component terminating remote from said common body in a ventricular electrode tip, an atrial component extending from said common body and normally reversely turning relative to said common body to assume a generally J-shaped configuration, said atrial component terminating remote from said common body in an atrial electrode tip, and releasable means carried by said atrial component for temporarily retaining said atrial component as a continuation of said common body and generally parallel to said ventricular component, said ventricular component having an enlargement flaring towards said common body and terminating in a shoulder, and said atrial component in its retained position lying axially behind said enlargement with said atrial electrode tip being disposed behind said shoulder.

5. An atrioventricular electrode according to claim 4 wherein said releasable means includes alignable apertures in said atrial electrode tip and said shoulder, and a projectable member extending from said atrial electrode tip into said shoulder aperture.

6. An atrioventricular electrode acording to claim 5 wherein said projectable member is in the form of a stylet for applying said atrioventricular electrode, said stylet extending from said atrial component through said common body.

7. An atrioventricular electrode according to claim 1 wherein said releasable means includes an apertured retainer, said atrial electrode tip having an aperture therethrough, and a projectable member extending through and from said atrial electrode tip into said apertured retainer.

8. An atrioventricular electrode according to claim 7 wherein said projectable member is in the form of a stylet for applying said atrioventricular electrode, said stylet extending from said atrial component through said common body.

* * * * *